(12) United States Patent
Iida

(10) Patent No.: US 8,012,757 B2
(45) Date of Patent: Sep. 6, 2011

(54) METHOD FOR PRODUCING STANDARD SAMPLE FOR USE IN QUANTITATIVE DETERMINATION OF RED PHOSPHORUS IN RESIN

(75) Inventor: Masuo Iida, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 13/062,036

(22) PCT Filed: May 24, 2010

(86) PCT No.: PCT/JP2010/058696

§ 371 (c)(1),
(2), (4) Date: Mar. 3, 2011

(87) PCT Pub. No.: WO2010/140496

PCT Pub. Date: Dec. 9, 2010

(65) Prior Publication Data

US 2011/0165686 A1    Jul. 7, 2011

(30) Foreign Application Priority Data

Jun. 3, 2009   (JP) ................. 2009-134086

(51) Int. Cl.
*G01N 1/28* (2006.01)
*G01N 31/00* (2006.01)
*G01N 31/12* (2006.01)

(52) U.S. Cl. .............. 436/17; 436/8; 436/103; 436/161; 436/174; 436/155

(58) Field of Classification Search .............. 436/8, 17, 436/103, 104, 161, 173, 174, 155; 149/29; 252/601
See application file for complete search history.

(56) References Cited

U.S. PATENT DOCUMENTS

| 2010/0120161 A1 | 5/2010 | Iida |
| 2010/0272610 A1 | 10/2010 | Iida |

FOREIGN PATENT DOCUMENTS

| JP | 59-031439 | 2/1984 |
| JP | 2004-161924 | 6/2004 |
| JP | 2009-36550 | 2/2009 |
| WO | WO 2008/133325 A1 | 11/2008 |

OTHER PUBLICATIONS

Iida et al. Analytical Sciences, vol. 24, Apr. 2008, pp. 539-542.*
Masuo Iida, et al., "Analysis of red phosphorus used as a flame retardant for polymer materials", Proceedings of Microelectronics Symposium, Sep. 18, 2008, vol. 18, pp. 127-130, JIEP.
Masuo Iida, et al., "Pyrolysis-gas chromatography mass spectrometry of red phosphorus in resins", SEI Technical Review, Jan. 2008, No. 172, pp. 30-33.

* cited by examiner

*Primary Examiner* — Maureen Wallenhorst
(74) *Attorney, Agent, or Firm* — McDermott Will & Emery LLP

(57) ABSTRACT

Provided are a method for preparing a standard sample in which a uniform dispersion of a predetermined concentration of red phosphorus is guaranteed even in a very small amount, and an analytical method for quantitatively determining red phosphorus contained in a resin by pyrolysis-GC/MS, in which the standard sample is used. The method for producing a standard sample for quantitatively determining red phosphorus contained in a resin includes the steps of preparing a red-phosphorus-containing compound by weighing a predetermined amount of red phosphorus and uniformly mixing the red phosphorus in a resin; decreasing the number of particles having a maximum diameter of 5 μm or more to ¹⁄₂₀ or less of the number of particles having a maximum diameter of 1 μm or more and less than 5 μm by pulverizing the red-phosphorus-containing compound; and obtaining a standard sample by weighing about 0.05 to 10 mg, preferably about 0.1 to 0.5 mg of the pulverized red-phosphorus-containing compound. The analytical method is a method for quantitatively determining red phosphorus contained in a resin by pyrolysis-GC/MS, in which the standard sample is used.

5 Claims, 3 Drawing Sheets

METHOD FOR PRODUCING STANDARD SAMPLE FOR USE IN QUANTITATIVE DETERMINATION OF RED PHOSPHORUS IN RESIN

RELATED APPLICATIONS

This application is the U.S. National Phase under 35 U.S.C. §371 of International Application No. PCT/JP2010/058696, filed on May 24, 2010, which in turn claims the benefit of Japanese Application No. 2009-134086, filed on Jun. 3, 2009, the disclosures of which Applications are incorporated by reference herein.

TECHNICAL FIELD

The present invention relates to a method for producing a standard sample that is necessary in quantitative analysis of red phosphorus contained in a resin (resin composition).

BACKGROUND ART

Recently, in consideration of environmental problems, non-halogen resin compositions in which a red-phosphorus flame retardant is blended with a non-halogen resin are used as flame-retarded resin compositions (Patent Literature 1). Consequently, the development of a method for analysis of red phosphorus useful for quality control in producing and shipping a product containing a red-phosphorus flame retardant, an acceptance inspection for purchasers of the product, and the like has been desired.

Red phosphorus is not dissolved in various types of solvents, and thus it is difficult to separate and collect red phosphorus. In addition, red phosphorus itself has no infrared absorption in an infrared spectrometer. Even when red phosphorus blended in a resin is analyzed using a Raman spectrometer, information about red phosphorus cannot be distinguished from the results. Furthermore, by an elemental analysis, for example, energy-dispersive X-ray (EDX) elemental analysis using an energy-dispersive X-ray fluorescence analyzer, discrimination between red phosphorus and organic phosphorus cannot be performed. Accordingly, in the case where organic phosphorus such as a phosphate ester may be contained, it is impossible to analyze red phosphorus only. Thus, red phosphorus contained in a resin cannot be analyzed by any of these methods.

Consequently, the inventor of the present invention developed, as a method for simply, rapidly, and reliably analyzing red phosphorus, in particular, red phosphorus contained in a resin as a flame retardant, a method in which a sample is gasified with a pyrolysis-gas chromatograph, and a measurement is then performed by gas chromatography, and furthermore, a mass spectrometer is used as means for detecting fractions of the gas chromatography, that is, an analytical method by pyrolysis-gas chromatography/mass spectrometry (pyrolysis-GC/MS), and proposed the method as Japanese Patent Application No. 2007-326840.

CITATION LIST

Patent Literature

Patent Literature 1: Japanese Unexamined Patent Application Publication No. 2004-161924

SUMMARY OF INVENTION

Technical Problem

In the quantitative determination of red phosphorus in a resin performed by pyrolysis-GC/MS or the like, a calibration curve is prepared in advance by calculating area values of a peak corresponding to a retention time of red phosphorus using standard substances containing predetermined concentrations of red phosphorus, and this calibration curve is compared with an area value of a peak at the same retention time of a measurement sample. Accordingly, in order to accurately perform the quantitative determination, it is necessary to appropriately prepare standard samples and to prepare an accurate calibration curve. However, as for the analysis using pyrolysis-GC/MS, it has been difficult to appropriately prepare these standard samples.

Specifically, in the analysis by pyrolysis-GC/MS, when the amount of sample increases, a problem such as contamination of a detector occurs. Therefore, the amount of sample is 10 mg at most, and usually 0.5 mg or less. In addition, unlike standard solution samples, the concentration of which can be adjusted by dilution, since the standard samples are also solid samples, it is difficult to ensure and guarantee a uniform dispersibility. That is, unlike an elemental analysis in which the amount of sample is often about 100 mg, since a very small amount of solid sample is used, it is very difficult to ensure and guarantee a uniform dispersibility even if any of existing kneading technologies is employed.

The present invention has been made in order to solve this problem in the related art, and an object of the present invention is to provide a method for producing a standard sample in which a uniform dispersion of a predetermined concentration of red phosphorus is guaranteed even in a very small amount in the range of about 0.05 to 10 mg, preferably about 0.1 to 0.5 mg. Also, another object of the present invention is to provide a method for quantitatively determining red phosphorus contained in a resin by pyrolysis-GC/MS, in which this standard sample is used, and with which an accurate quantitative determination can be realized.

Solution to Problem

As a result of intensive studies conducted in order to solve the above problem, the inventor of the present invention has found that, by kneading a predetermined amount of red phosphorus in a resin to prepare a red-phosphorus-containing compound, and finely pulverizing the compound, it is possible to obtain a standard sample in which a uniform dispersion of a predetermined concentration of red phosphorus is guaranteed even in a very small amount in the range of about 0.05 to 10 mg, preferably about 0.1 to 0.5 mg, and completed the present invention.

Specifically, the present invention provides, as a first aspect of invention of the present application thereof, a method for producing a standard sample for quantitatively determining red phosphorus contained in a resin, the method including the steps of:

preparing a red-phosphorus-containing compound by weighing a predetermined amount of red phosphorus and uniformly mixing the red phosphorus in a resin;

decreasing the number of particles having a maximum diameter of 5 μm or more to 1/20 or less of the number of particles having a maximum diameter of 1 μm or more and less than 5 μm by pulverizing the red-phosphorus-containing compound; and obtaining a standard sample by weighing 0.05 to 10 mg of the pulverized red-phosphorus-containing compound.

To prepare the red-phosphorus-containing compound, it is necessary to sufficiently uniformly blend (knead) red phosphorus in the resin. In addition, it is necessary to perform the preparation under the condition that the red phosphorus during the blending (kneading) does not sublime. Accordingly, it is necessary to determine the blending temperature to be not higher than 400° C., which is the sublimation temperature of red phosphorus, and not lower than a temperature (melting point) at which the resin can be melted. The type of resin used and the blending method are not particularly limited so long as a uniform kneading is ensured and the prepared compound is pulverized and can be used as a sample for pyrolysis-GC/MS.

The amount of red phosphorus kneaded in the resin is appropriately selected in accordance with a measurement range of the concentration of red phosphorus in a sample. For example, when the concentration of red phosphorus contained in a measurement target sample is assumed to be in the range of 100 to 1,000 ppm, the amounts of red phosphorus respectively corresponding to several points (for example, 100, 300, 500, 700, and 1,000 ppm) within this range are selected so that a calibration curve in the range of 100 to 1,000 ppm can be prepared.

The step of pulverizing the red-phosphorus-containing compound is a so-called fine pulverization, and the red-phosphorus-containing compound is pulverized until the number of particles having a maximum diameter of 5 μm or more is 1/20 or less of the number of particles having a maximum diameter of 1 μm or more and less than 5 μm. For the purpose of a more accurate quantitative determination, the number of particles having a maximum diameter of 5 μm or more is preferably smaller, and a case where particles having a maximum diameter of 5 μm or more are not contained is particularly preferable. When the shape of the pulverized fine particles is not a spherical shape, the particle diameter varies depending on the measurement direction. However, the term "maximum diameter" refers to the maximum among diameters when the diameter is measured in all directions.

The red-phosphorus-containing compound that has been finely pulverized in this manner is weighed in an amount of 0.05 to 10 mg to obtain a standard sample. Since the finely pulverized red-phosphorus-containing compound is mainly composed of fine particles having a maximum diameter of less than 5 μm, even in a very small amount of 0.05 to 10 mg, a uniform dispersion of red phosphorus in the standard sample is guaranteed.

An invention described in a second aspect of invention of the present application is the method for producing the standard sample for quantitatively determining red phosphorus contained in the resin described in a first aspect of invention of the present application, wherein, in the step of obtaining the standard sample, 0.1 to 0.5 mg of the pulverized red-phosphorus-containing compound is weighed. The amount of red-phosphorus-containing compound is preferably 0.5 mg or less in order to suppress contamination of a detector or the like, and is preferably 0.1 mg or more in order to obtain a more accurate calibration curve. Since the finely pulverized red-phosphorus-containing compound is mainly composed of fine particles having a maximum diameter of less than 5 μm, even in a very small amount of 0.1 to 0.5 mg, a uniform dispersion of red phosphorus in the standard sample is guaranteed.

An invention described in a third aspect of invention of the present application is the method for producing the standard sample for quantitatively determining red phosphorus contained in the resin described in a first or a second aspect of invention of the present application, wherein the red-phosphorus-containing compound is pulverized by striking the compound and applying a shear stress to the compound.

Hitherto, pulverization of a resin compound has been conducted by striking the compound with a hammer, crushing the compound with a mortar, or the like. With this method, however, it is impossible to perform pulverization until the pulverized resin compound is mainly composed of fine particles having a maximum diameter of less than 5 μm. However, by striking a resin compound and applying a shear stress to the resin compound, the resin compound can be finely pulverized until the pulverized resin compound is mainly composed of fine particles having a maximum diameter of less than 5 μm. In particular, a method in which crushing and pulverizing are performed while striking a resin compound and applying a shear stress to the resin compound with a three-dimensional eight-figure motion is preferable.

The present invention provides, in addition to the method for producing the standard sample, a method for quantitatively determining red phosphorus contained in a resin, wherein this standard sample is used. Specifically, the present invention provides a method for quantitatively determining red phosphorus contained in a resin, the method including the steps of:

producing a plurality of standard samples, the red phosphorus contents of which are varied, by the method for producing the standard sample for quantitatively determining red phosphorus contained in the resin described in any one of first to third aspects of invention of the present application;

pyrolyzing each of the standard samples to gasify the samples, separating each of the pyrolyzed samples into fractions by gas chromatography, and obtaining a peak intensity ratio by dividing a peak area value obtained with respect to a fraction of a retention time corresponding to red phosphorus by a sample weight;

preparing a calibration curve showing the relationship between the peak intensity ratio and the red phosphorus content;

pyrolyzing a measurement target sample to gasify the sample, separating the pyrolyzed sample into fractions by gas chromatography, and obtaining a peak intensity ratio A with respect to a fraction corresponding to red phosphorus; and determining a red phosphorus content corresponding to the peak intensity ratio A using the calibration curve (a fourth aspect of invention of the present application).

Herein, the term "peak area value" refers to a peak area or peak height obtained with a detector. The detector is not particularly limited, and any detector commonly used in GC can be used. Preferably, a mass spectrometer (MS) is used. When the detector is a mass spectrometer, the peak area value is a value of a peak area or peak height of all ions or selected one or a plurality of ions in an ion chromatogram.

The retention time corresponding to red phosphorus varies depending on the measurement conditions. Therefore, it is preferable to determine the retention time in advance by conducting a measurement of elemental red phosphorus under the same conditions. In this quantitative method, the standard sample obtained by the method for producing a standard sample of the present invention, that is, the standard sample in which a uniform dispersibility of red phosphorus is ensured is used, and thus an accurate calibration curve is prepared and red phosphorus contained in a resin can be quantitatively determined accurately.

Advantageous Effects of Invention

According to the method for producing a standard sample for quantitatively determining red phosphorus contained in a resin of the present invention, it is possible to obtain a standard sample in which a uniform dispersion of a predetermined concentration of red phosphorus is guaranteed even in a very small amount of about 0.05 to 10 mg, preferably about 0.1 to 0.5 mg. Accordingly, this method is suitable as a method for producing a standard sample for pyrolysis-GC/MS, in which the amount of sample is about 0.05 to 10 mg, preferably about 0.1 to 0.5 mg. In addition, red phosphorus contained in a resin can be quantitatively determined accurately by the method for quantitatively determining red phosphorus contained in a resin of the present invention, in which the standard sample thus obtained is used.

DESCRIPTION OF EMBODIMENTS

Figure 1:
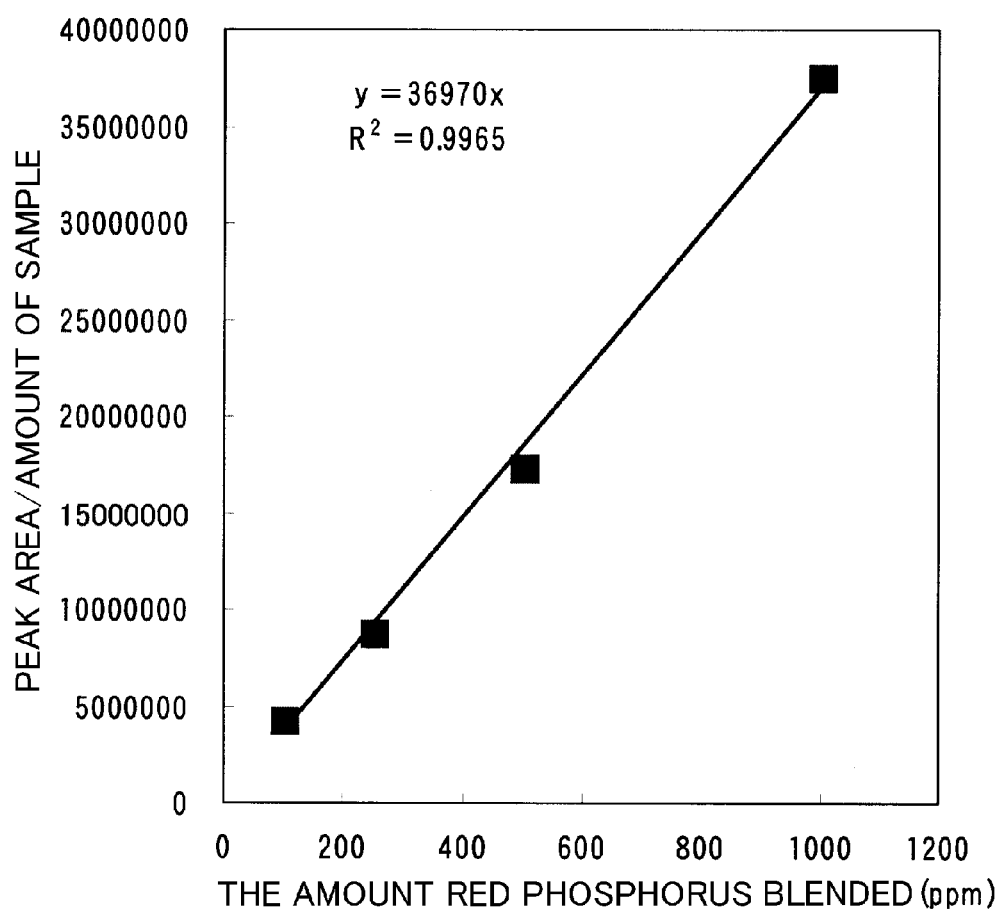
FIG. 1 is a graph showing the relationship between the red phosphorus content and a peak intensity ratio of a GC/MS spectrum.

Next, embodiments for carrying out the present invention will be described.

A mixing method used in a step of preparing a red-phosphorus-containing compound is not particularly limited. Examples of the method include methods using a press kneader, a roll mixer, a twin-screw mixer, or a Banbury mixer. Examples of a resin that can be used include various types of resins such as thermoplastic resins, thermosetting resins, and rubbers.

Here, examples of the thermoplastic resins include polyethylene, polypropylene, polymethylpentene, polybutene, crystalline polybutadiene, polystyrene, polybutadiene, styrene-butadiene resins, polyvinyl chloride, polyvinyl acetate, polyvinylidene chloride, ethylene-vinyl acetate copolymers (ethylene-vinyl acetate (EVA), acrylonitrile-styrene (AS), acrylonitrile-butadiene-styrene (ABS), ionomers, acrylonitrile-acrylate-styrene (AAS), and acrylonitrile-chlorinated polyethylene-styrene (ACS)), polymethylmethacrylate, polytetrafluoroethylene, ethylene-tetrafluoroethylene copolymers, polyoxymethylene, polyamide, polycarbonate, polyphenylene ether, polyethylene terephthalate, polybutylene terephthalate, polyarylate (U-polymer), polystyrene, polyethersulfone, polyimide, polyamideimide, polyphenylene sulfide, polyoxybenzoyl, polyether ether ketone, polyetherimide, cellulose acetate, cellulose acetate butyrate, cellophane, and celluloid. Elastomers such as styrene-butadiene thermoplastic elastomers, polyolefin thermoplastic elastomers, urethane thermoplastic elastomers, polyester thermoplastic elastomers, and polyamide thermoplastic elastomers can also be used.

Examples of the thermosetting resins include formaldehyde resins, phenol resins, amino resins (urea resins, melamine resins, and benzoguanamine resins), unsaturated polyester resins, diallyl phthalate resins, alkyd resins, epoxy resins, urethane resins (polyurethanes), and silicon resins (silicone).

As for the fine pulverization of the red-phosphorus-containing compound, as described above, it is preferable to use a method of performing crushing and pulverizing by striking each sample and applying a shear stress to the sample with a three-dimensional eight-figure motion. Since the degree of crushing and the crushing capacity vary depending on the type of crushing medium, the number of vibrations, the crushing time, and the like, it is preferable to use an apparatus in which conditions such as the number of vibrations and the crushing time can be freely adjusted. An example of such an apparatus is a multi-sample precision sample pulverizer that is commercially available as a trade name "Multi-beads shocker" (manufactured by Yasui Kikai Corporation).

In the method of quantitatively determining red phosphorus contained in a resin of the present invention, the step of pyrolyzing a standard sample or a measurement sample to gasify the sample is performed by heating the sample to a temperature at which the sample is gasified or higher. Accordingly, the heating temperature is not lower than the sublimation temperature (416° C.) of red phosphorus. However, in order to reliably sublime red phosphorus and to perform analysis with a high accuracy, it is necessary to heat at a temperature equal to or higher than the decomposition temperature of the resin. The heating temperature is preferably about 600° C. to 800° C.

The heating time is not shorter than a time necessary for completely gasify the sample. The heating time varies depending on the heating temperature, the amount of sample, and the like, and is not particularly limited. Heating means is not particularly limited, and any heating means used in a usual pyrolysis-gas chromatograph can be used.

The sample pyrolyzed and gasified is introduced into a column of a gas chromatograph. Components in the sample are separated in accordance with a difference in the distribution equilibrium constant from that of a stationary phase, and eluted at times (retention times) that differ for respective components. Conditions for this gas chromatography are the same as conditions for usual pyrolysis-gas chromatography used in analysis of resins.

Either a packed column or a capillary column can be used as the column, but a capillary column is preferably used in qualitative analysis.

The sample eluted from the column of the gas chromatograph is introduced into a detector, and the presence or absence of elusion (fraction) in accordance with the retention time is detected. The analysis of red phosphorus is performed by detecting a fraction at a retention time corresponding to red phosphorus. For example, if a detection peak (fraction) is present at a retention time corresponding to red phosphorus, it is confirmed that red phosphorus is present in the sample.

The retention time corresponding to red phosphorus varies depending on operating conditions for the pyrolysis-gas chromatograph, the type of column, and the like. Therefore, prior to the measurement of a sample, the same analysis as that described above is performed using standard samples of red phosphorus so that the retention time corresponding to red phosphorus is determined in advance.

As described above, a mass spectrometer (MS) is preferably used as the detector. According to mass spectrometry, red phosphorus shows characteristic peaks at m/z=31, 62, 93, and 124. A calibration curve is prepared on the basis of the area of a peak or the height of a peak obtained from the standard samples, and a measurement sample is then measured. Quantitative analysis is performed on the basis of the calibration curve and the area of a peak obtained by the measurement of the sample.

The mass spectrometer includes an interfacing unit, which is a portion connected to the column of the gas chromatograph, an ion source that performs ionization of a sample, a mass separation unit, a detector, and the like. As an ionization method in the ion source, either an electron impact ionization (EI) method or a chemical ionization (CI) method can be employed. As an analyzer of the mass separation unit, either a magnetic sector-type analyzer or a quadrupole-type analyzer can be used. Furthermore, as a measurement mode in the detector, either the SCAN mode or the SIM mode can be used.

Next, embodiments for carrying out the present invention will be described by way of Example, but the scope of the present invention is not limited to only the Example.

EXAMPLE

[Preparation of Red-Phosphorus-Containing Compound]

A red phosphorus reagent manufactured by KANTO CHEMICAL CO., INC. was used as red phosphorus. This red phosphorus was added to an ethylene-ethyl-acrylate copolymer (EEA, trade name: EVAFLEX A701) so that the red phosphorus content was 100, 250, 500, or 1,000 ppm. Each of the mixtures was mixed with a roll mixer at 200° C. for five minutes to prepare four red-phosphorus-containing compounds, the red phosphorus contents of which were different from each other.

[Fine Pulverization of Red-Phosphorus-Containing Compound]

Figure 2:
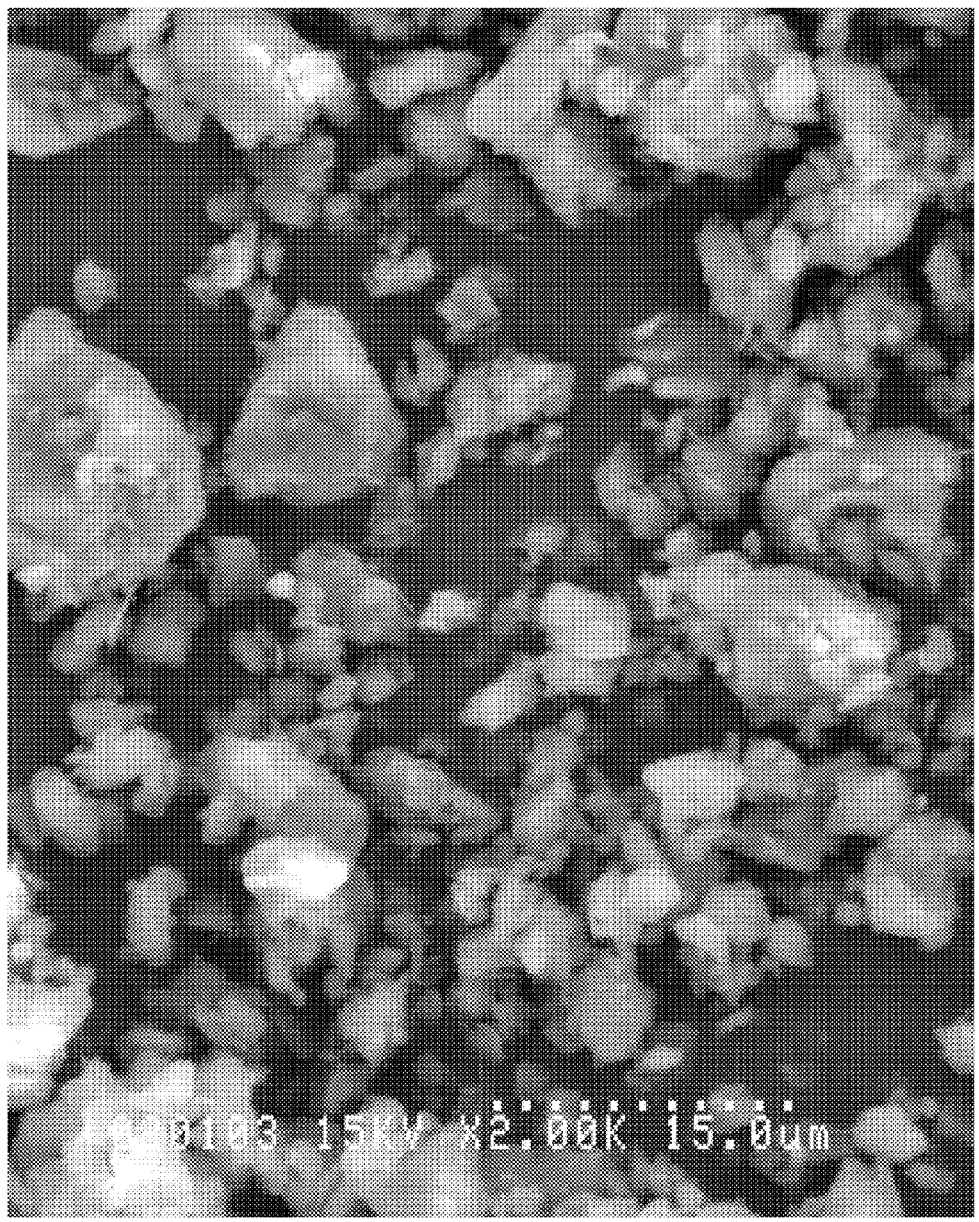
FIG. 2 is a scanning electron microscope (SEM) photograph of a pulverized product obtained in Example.

Each of the prepared red-phosphorus-containing compounds was finely pulverized with a multi-sample precision sample pulverizer (trade name: Multi-beads shocker manufactured by Yasui Kikai Corporation). Specifically, 1 g of each of the prepared four red-phosphorus-containing compounds was put in a 40-mL titanium pulverization container, and was pulverized under a liquid nitrogen condition at a number of vibrations of 3,000 rpm for 60 seconds. As a result, pulverized products were obtained in which the number of particles having a maximum diameter of 5 μm or more is 1/20 or less of the number of particles having a maximum diameter of 1 μm or more and less than 5 μm. FIG. 2 shows a SEM photograph of the pulverized product.

[Measurement of Pyrolysis-GC/MS and Preparation of Calibration Curve]

About 0.5 mg of each of the pulverized products thus obtained was weighed. Each of the samples was pyrolyzed (gasified) with the pyrolyzer under the pyrolysis conditions described below. The gasified sample was measured with gas chromatograph/mass spectrometry (GC/MS apparatus) described below. A peak area value for a peak at a retention time of 4.2 minutes was determined, and a ratio peak area value/measurement sample weight (hereinafter referred to as "peak intensity ratio") was calculated. Mass spectrometry (MS) was conducted for the peak at the retention time of 4.2 minutes of the gas chromatograph obtained under these measurement conditions. As a result, peaks were obtained at positions of m/z=62, 93, and 124. Accordingly, the peak at a retention time of 4.2 minutes was identified as a peak of red phosphorus. In addition, according to a measurement result of pyrolysis-GC/MS conducted using elemental red phosphorus under the same conditions as those described above, the peak of the elemental red phosphorus was observed at a retention time of 4.2 minutes.

(Pyrolysis Condition)

A pyrolyzer manufactured by Frontier Laboratories Ltd. was used. The pyrolysis condition was 600° C.×0.2 minutes.

(GC/MS Apparatus)

An Agilent 6890 manufactured by Agilent Technologies, Inc. was used. Operating conditions for this apparatus are described below.

Column: HP-5MS (inner diameter: 0.25 mm, film thickness: 0.25 mm, length: 30 m)

Column flow rate: Helium (He) gas 1.0 mL/min

Temperature-increasing condition: The temperature was increased from 50° C. to 320° C. at a rate of 25° C./min and maintained at 320° C. for five minutes.

MS temperature: 230° C. (MS Source), 150° C. (MS Quad)

Interfacing unit temperature: 280° C.

Measurement mode: SCAN mode

Note that the measurement by mass spectrometry (MS) was performed in the range of m/z=33 to 550 in order to avoid peaks of oxygen.

The measurement was conducted for each sample three times. The results are shown in Table I.

TABLE I

|  |  | The amount of red phosphorus blended (ppm) | | | |
|---|---|---|---|---|---|
|  |  | 100 | 250 | 500 | 1000 |
| n = 1 | Peak area: A | 2168723 | 4860241 | 8491186 | 19768462 |
|  | Amount of sample (mg): B | 0.53 | 0.51 | 0.52 | 0.52 |
|  | Peak intensity ratio A/B | 4091930 | 9529884 | 16329204 | 38016273 |
| n = 2 | Peak area: A | 2515051 | 4489632 | 8932955 | 18222040 |
|  | Amount of sample (mg): A | 0.52 | 0.51 | 0.53 | 0.51 |
|  | Peak intensity ratio A/B | 4836637 | 8803200 | 16854632 | 35729490 |
| n = 3 | Peak area: A | 2096525 | 4037944 | 9632003 | 19495334 |
|  | Amount of sample (mg): B | 0.51 | 0.50 | 0.51 | 0.50 |
|  | Peak intensity ratio A/B | 4110833 | 8075888 | 18886280 | 38990668 |
|  | Average | 4346467 | 8802991 | 17356705 | 37578810 |
|  | Standard deviation | 424605 | 726998 | 1350451 | 1674022 |
|  | cv | 9.8% | 8.3% | 7.8% | 4.5% |

* The "peak area: A" represents an area value (signal intensity) of a peak at a retention time of 4.2 minutes corresponding to red phosphorus in a total ion chromatogram As shown in Table I, the variation (cv) in the peak intensity ratio in the measurement that was performed three times was in the range of 4.5% (in the case where the amount of red phosphorus blended was 1,000 ppm) to 9.8% (in the case where the amount of red phosphorus blended was 100 ppm). FIG. 1 is a graph showing the relationship between the red phosphorus content (the amount of red phosphorus blended) in the resin and the average of the peak intensity ratios measured three times. As is apparent from FIG. 1, there is a good relationship between the red phosphorus content in the resin and the peak intensity ratio in the GC/MS analysis, and the correlation coefficient thereof was 0.9965. This result showed that a quantitative analysis with a high accuracy could also be performed by the quantitative analytical method of the present invention.

Comparative Example

Figure 3:
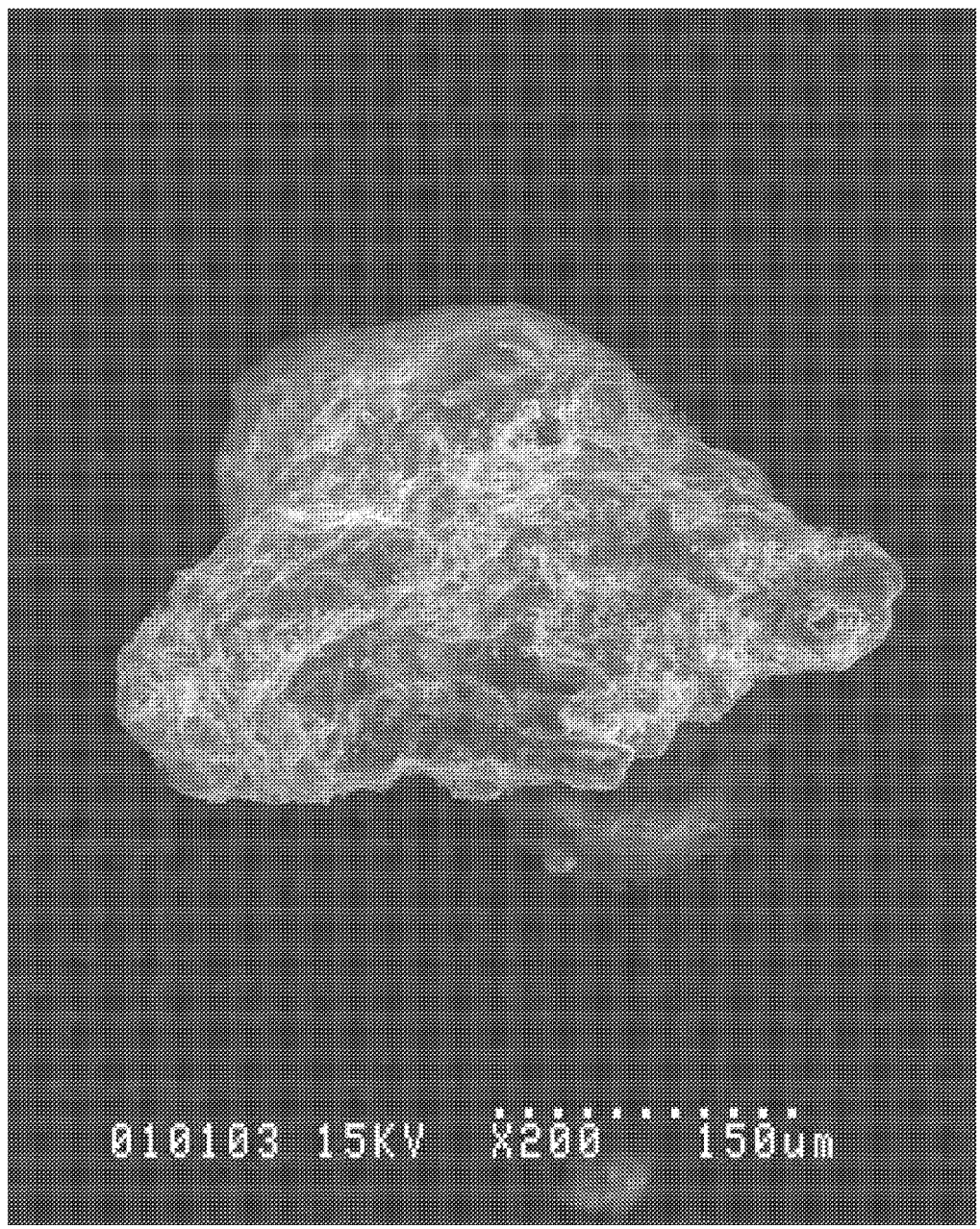
FIG. 3 is a SEM photograph of a pulverized product obtained in Comparative Example.

A pyrolysis-GC/MS measurement was conducted as in Example except that pulverized products prepared by pulverizing the red-phosphorus-containing compounds using a conventional pulverizer were used instead of using the pulverized products prepared by finely pulverizing the red-phosphorus-containing compounds. FIG. 3 shows a SEM image of the pulverized product. Furthermore, Table II shows the results when the measurement was conducted for each sample three times.

TABLE II

|  |  | The amount of red phosphorus blended (ppm) | | | |
| --- | --- | --- | --- | --- | --- |
|  |  | 100 | 250 | 500 | 1000 |
| n = 1 | Peak area: A | 1168723 | 476041 | 8491186 | 9768462 |
|  | Amount of sample (mg): B | 0.54 | 0.57 | 0.52 | 0.55 |
|  | A/B | 2164302 | 835160 | 16329204 | 17760840 |
| n = 2 | Peak area: A | 3045051 | 2489632 | 8932955 | 13822040 |
|  | Amount of sample (mg): B | 0.52 | 0.55 | 0.58 | 0.51 |
|  | A/B | 5855867 | 4526604 | 15401647 | 27102039 |
| n = 3 | Peak area: A | 2095525 | 2437944 | 2632003 | 25495334 |
|  | Amount of sample (mg): B | 0.56 | 0.50 | 0.56 | 0.50 |
|  | A/B | 3742009 | 4875888 | 4700005 | 50990668 |
|  | Average | 3920726 | 3412550 | 12143619 | 31951182 |
|  | Standard deviation | 1852260 | 2238908 | 6463020 | 17137415 |
|  | cv | 47.2% | 65.6% | 53.2% | 53.6% |

As shown in Table II, the variation (cv) in the peak intensity ratio in the measurement that was performed three times was in the range of 47.2% (in the case where the amount of red phosphorus blended was 100 ppm) to 65.6% (in the case where the amount of red phosphorus blended was 250 ppm), which was significantly larger than that of Example (example of the present invention). The comparison between Example and Comparative Example shows that, according to the present invention, quantitative determination of ref phosphorus contained in a resin can be performed with an accuracy significantly higher than that in the related art.

Reference Example 1

A pyrolysis-GC/MS measurement was conducted using an elemental red phosphorus reagent in a sample amount of about 0.1 mg instead of using a red-phosphorus-containing compound. Table III shows the results when the measurement was conducted three times.

TABLE III

|  |  | Elemental red phosphorus reagent |
| --- | --- | --- |
| n = 1 | Peak area: A | 513955782 |
|  | Amount of sample (mg): B | 0.10 |
|  | A/B | 5139557820 |
| n = 2 | Peak area: A | 587265799 |
|  | Amount of sample (mg): B | 0.11 |
|  | A/B | 5338779991 |
| n = 3 | Peak area: A | 671866809 |
|  | Amount of sample (mg): B | 0.12 |
|  | A/B | 5598890075 |
|  | Average | 5359075962 |
|  | Standard deviation | 230337741 |
|  | cv | 4.3% |

As shown in Table III, even in the measurement of the elemental red phosphorus, the variation (cv) was 4.3%, which shows that this analytical method itself causes a variation of about 5%. From the comparison between this result and the results shown in Table I, it is clear that the variations in the concentration in the standard samples in Example are very small.

The invention claimed is:

1. A method for producing a standard sample for quantitatively determining red phosphorus contained in a resin, the method comprising the steps of:
    preparing a red-phosphorus-containing compound by weighing a predetermined amount of red phosphorus and uniformly mixing the red phosphorus in a resin;
    decreasing the number of particles having a maximum diameter of 5 μm or more to 1/20 or less of the number of particles having a maximum diameter of 1 μm or more and less than 5 μm by pulverizing the red-phosphorus-containing compound; and
    obtaining a standard sample by weighing 0.05 to 10 mg of the pulverized red-phosphorus-containing compound.

2. The method for producing the standard sample for quantitatively determining red phosphorus contained in the resin according to claim 1, wherein, in the step of obtaining the standard sample, 0.1 to 0.5 mg of the pulverized red-phosphorus-containing compound is weighed.

3. The method for producing the standard sample for quantitatively determining red phosphorus contained in the resin according to claim 2, wherein the red-phosphorus-containing compound is pulverized by striking the compound and applying a shear stress to the compound.

4. The method for producing the standard sample for quantitatively determining red phosphorus contained in the resin according to claim 1, wherein the red-phosphorus-containing compound is pulverized by striking the compound and applying a shear stress to the compound.

5. A method for quantitatively determining red phosphorus contained in a resin, the method comprising the steps of:
    producing a plurality of standard samples, the red phosphorus contents of which are varied, by the method for producing the standard sample for quantitatively determining red phosphorus contained in the resin according to any one of claims 1 to 3;
    pyrolyzing each of the standard samples to gasify the samples, separating each of the pyrolyzed samples into fractions by gas chromatography, and obtaining a peak intensity ratio by dividing a peak area value obtained with respect to a fraction of a retention time corresponding to red phosphorus by a sample weight;
    preparing a calibration curve showing the relationship between the peak intensity ratio and the red phosphorus content;

pyrolyzing a measurement target sample to gasify the sample, separating the pyrolyzed sample into fractions by gas chromatography, and obtaining a peak intensity ratio A with respect to a fraction corresponding to red phosphorus; and determining a red phosphorus content corresponding to the peak intensity ratio A using the calibration curve.

* * * * *